United States Patent [19]

Hittinger

[11] Patent Number: 5,578,739
[45] Date of Patent: Nov. 26, 1996

[54] PROCESS FOR THE PREPARATION OF BACCATIN III AND 10-DEACETYLBACCATIN III DERIVATIVES

[75] Inventor: Augustin Hittinger, Igny, France

[73] Assignee: Rhone-Poulenc Rorer S.A., Antony, France

[21] Appl. No.: 498,613

[22] Filed: Jul. 6, 1995

Related U.S. Application Data

[63] Continuation of Ser. No. 175,380, filed as PCT/FR92/00649, Jul. 8, 1992 published as WO93/01179, Jan. 21, 1993, abandoned.

[30] Foreign Application Priority Data

Jul. 10, 1991 [FR] France .................................. 91 08673

[51] Int. Cl.$^6$ .............................................. C07D 305/14
[52] U.S. Cl. .................................... 549/510; 549/511
[58] Field of Search ............................... 549/510, 511

[56] References Cited

U.S. PATENT DOCUMENTS 4,924,012  5/1990  Colin et al. ........................... 549/510

OTHER PUBLICATIONS

Auerbach et al, J.C.S. Chem. Comm., pp. 298–299, 1974.
Hannessian et al, Can. J. Chem., vol. 53, pp. 2975–2977, 1975.
Denis et al, J. Am. Chem. Soc., vol. 110, pp. 5917–5919, 1988.
J. Am. Chem. Soc. 1988, 110, 5917–5919, J. N.–Denis et al. "A Highly Efficient, Practical Approach to Natural Taxol".
Tetrahedron vol. 42, No. 16, pp. 4451–4460, 1986, "Chemical Studies of 10–Deacetyl Baccatin III, Hemisynthesis of Taxol Derivatives", F. Gueritte–Voegelein et al.

J. Org. Chem. 1986 51, 3239–3242, N. F. Nagri et al. "Modified Taxols 3. Preparation and Acylation of Baccatin III".

*Primary Examiner*—Ba K. Trinh
*Attorney, Agent, or Firm*—Finnegan, Henderson, Farabow, Garrett & Dunner

[57] ABSTRACT

This invention relates to process for the preparation of a taxane derivative of general formula (I):

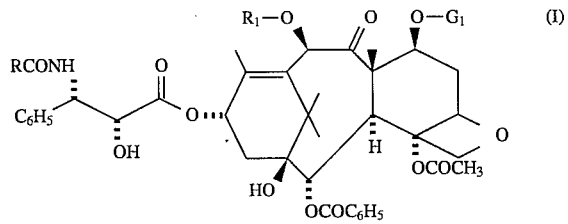

and use of the product obtained for the preparation of taxane derivatives of general formula (II):

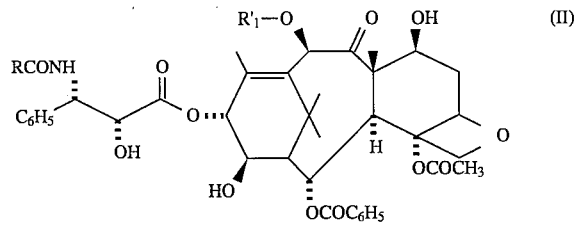

In the general formula (I), $R_1$ is an acetyl radical or a protective grouping $G_1$ is a protective grouping and R is a t-butoxy or phenyl radical. In the general formula (II), R is a t-butoxy or phenyl radical and $R'_1$ is a hydrogen atom or an acetyl radical.

10 Claims, No Drawings

PROCESS FOR THE PREPARATION OF BACCATIN III AND 10-DEACETYLBACCATIN III DERIVATIVES

This is a continuation of application Ser. No. 08/175,380, filed on Jan. 10, 1994, now abandoned, which is a 371 of PCT/FR92/00649 dated Jul. 8, 1992, published as WO93/01179, Jan. 21, 1993.

DESCRIPTION OF THE INVENTION

The present invention relates to a process for the preparation of derivatives of baccatin III and of 10-deacetylbaccatin III, of general formula:

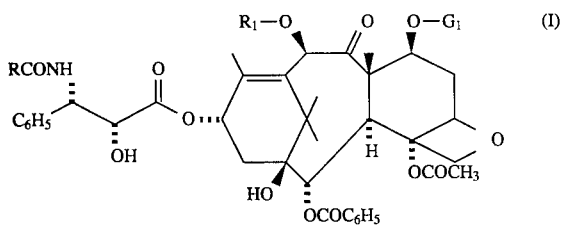

in which R represents a tert-butoxy or phenyl radical, $R_1$ represents an acetyl radical or a protecting group of the hydroxyl functional group in the form of an ether, ester or carbonate and $G_1$ represents a protecting group of the hydroxyl functional group in the form of an ether, ester or carbonate in the 2'R,3'S or 2'S,3'S form.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

More particularly, the present invention relates to a process for the preparation of a product of general formula (I) in which R represents a tertbutoxy or phenyl radical, $R_1$ represents an acetyl or 2,2,2-trichloroethoxycarbonyl radical and $G_1$ represents a 2,2,2-trichloroethoxycarbonyl radical, in the 2'R,3'S or 2'S,3'S form.

The products of general formula (I) are particularly useful in the synthesis of the products of general formula:

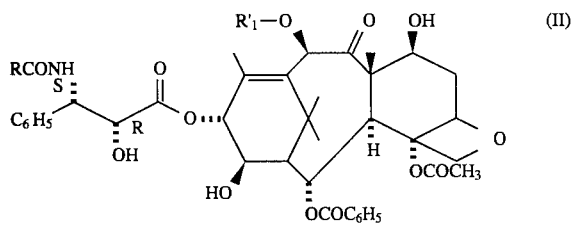

in which R is defined as previously and $R'_1$ represents a hydrogen atom or an acetyl radical.

The products of general formula (II) in which R represents a phenyl radical correspond to taxol and 10-deacetyltaxol and the products of general formula (II) in which R represents a tert-butoxy radical correspond to those which are the subject of European Patent EP 0,253,738.

The products of general formula (II) show particularly advantageous antitumor and antileukaemic activities.

The products of general formula (I) in which R represents a tert-butoxy radical can be obtained under the conditions described in European Patent EP 0,253,738 after separation of the products arising from the hydroxyamination of a product of general formula:

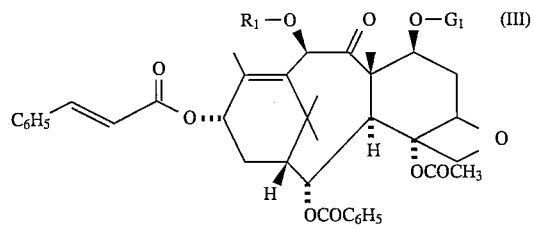

in which $R_1$ represents an acetyl or 2,2,2-trichloroethoxycarbonyl radical and $G_1$ represents a 2,2,2-trichloroethoxycarbonyl radical.

The products of general formula (I) in which R represents a tert-butoxy radical are converted to corresponding products of general formula (II) by removal of the protecting groups represented by $R_1$ and $G_1$. More particularly, when $R_1$ and $G_1$ represent a 2,2,2-trichloroethoxycarbonyl radical, this replacement is carried out by the action of zinc in the presence of acetic acid at a temperature of between 30° and 60° C. or by means of an inorganic or organic acid such as hydrochloric acid or acetic acid in solution in an aliphatic alcohol containing 1 to 3 carbon atoms in the presence of zinc under the conditions described in European Patent EP 0,253,738.

The preparation of the products of general formula (II) is known from American Patents U.S. Pat. No. 4,924,011 and U.S. Pat. No. 4,924,012, by condensation of a β-phenylisoserine derivative of general formula:

in which R is defined as previously and $R_2$ represents a protecting group of the hydroxyl functional group chosen especially from the methoxymethyl, 1-ethoxyethyl, benzyloxymethyl, (β-trimethylsilylethoxy)methyl, tetrahydropyranyl or 2,2,2-trichloroethoxycarbonyl radicals, with a baccatin III or 10-deacetylbaccatin III derivative of general formula:

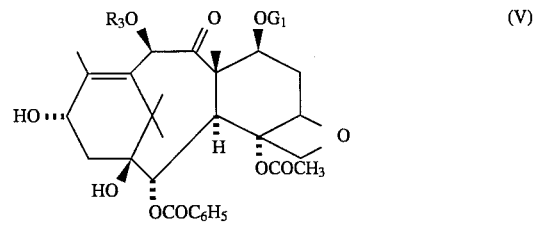

in which $R_3$ represents an acetyl radical or a protecting group of the hydroxyl functional group chosen from the 2,2,2-trichloroethoxycarbonyl radical or from trialkylsilyl radicals, each alkyl part of which contains 1 to 3 carbon atoms, and $G_1$ represents a protecting group of the hydroxyl functional group chosen from the 2,2,2-trichloroethoxycarbonyl radical or from trialkylsilyl radicals, each alkyl part of which contains 1 to 3 carbon atoms, followed by the replacement of the protecting groups of the hydroxyl functional groups by hydrogen atoms.

Depending on the nature of the protecting groups, this replacement can be carried out by means of zinc in the presence of acetic acid or of an inorganic or organic acid such as hydrochloric acid or acetic acid in solution in an aliphatic alcohol containing 1 to 3 carbon atoms in the presence of zinc when the protecting groups represent at least one 2,2,2-trichloroethoxycarbonyl radical, or by means of an acid such as hydrochloric acid in an aliphatic alcohol containing 1 to 3 carbon atoms at a temperature of approximately 0° C. when the protecting groups represent at least one trialkylsilyl radical.

The products of general formula (II) obtained by the implementation of these previously known processes must be purified, generally by chromatography or by crystallization, in order, more particularly, to separate the 2'R,3'S and 2'S,3'S epimers. This separation is difficult to carry out industrially due to the cytotoxicity of the products of general formula (II).

It has now been found that practically pure products of general formula (II) can be obtained by prior purification of a product of general formula (I) and then by removal of the protecting groups represented by $R_1$ and $G_1$, under non-epimerizing conditions, from the purified products of general formula (I).

The present invention relates to a process for the preparation of a product of general formula (I) from a taxane derivative of general formula:

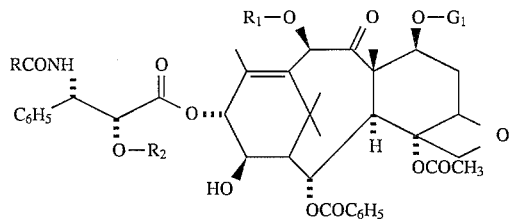

in which $R_1$ and $G_1$ are defined as previously and $R_2$ represents a protecting group of the hydroxyl functional group chosen from the methoxymethyl, 1-ethoxyethyl, benzyloxymethyl, (β-trimethylsilylethoxy)methyl or tetrahydropyranyl radicals, by treatment in acid medium at a temperature of between 0° and 30° C. Generally, an alcoholic solution of a strong inorganic acid is used. Preferably, an ethanolic solution of hydrochloric acid is used.

The product of general formula (II) is obtained by treating the product of general formula (I) in which $R_1$ represents an acetyl or 2,2,2-trichloroethoxycarbonyl radical and $G_1$ represents a 2,2,2-trichloroethoxycarbonyl radical, in the purified 2'R,3'S or 2'S,3'S form, generally purified by chromatography or crystallization, with zinc in acetic acid in an alcoholic medium at a temperature of between 20° C. and the reflux temperature of the reaction mixture. Preferably, the temperature is approximately 65° C.

The product of general formula (VI) can be obtained by the action of an acid of general formula:

on a baccatin III or 10-deacetylbaccatin III derivative of general formula:

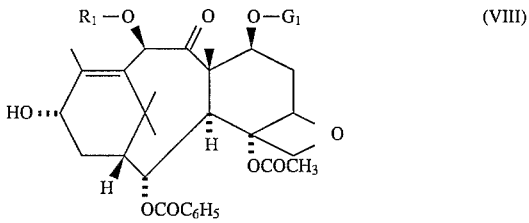

in which $R_1$ and $G_1$ are defined as previously, under the conditions described in American Patents U.S. Pat. No. 4,924,011 and U.S. Pat. No. 4,924,012.

As the products of general formula (I) are devoid of cytotoxicity, their purification by chromatography or crystallization does not require any particular safety and industrial hygiene measures.

EXAMPLES

The following examples, given without implied limitation, show how the invention can be put into practice.

EXAMPLE 1

23 g of 4-acetoxy-2α-benzoyloxy-5β,20-epoxy-1β-hydroxy-9-oxo-7β,10β-bis(2,2,2-trichloroethoxy)carbonyloxy-11-taxen-13α-yl (2R,3S)-3-tert-butoxycarbonylamino-2-(1-ethoxyethoxy)-3-phenylpropionate, 200 cm³ of methanol and 18.7 cm³ of 1N ethanolic hydrochloric acid are introduced, under an argon atmosphere, into a 500 cm³, round-bottomed flask equipped with a stirrer and a dropping funnel. The mixture is stirred for 30 minutes at a temperature of approximately 20° C. After concentrating the reaction mixture under reduced pressure at a temperature of less than 25° C. until a not totally dry residue (40 g) is obtained, the residue is taken up with 200 cm³ of methylene chloride and then washed with 100 cm³ of a saturated solution of sodium chloride. After drying over sodium sulphate, filtering and concentrating to dryness under reduced pressure (25 mm of mercury; 3.3 kPa, then 1 mm of mercury; 0.13 kPa) at 25° C., a colorless oil (25 g) is obtained which is purified by chromatography on 610 g of silica (40–63 μm), eluting with a cyclohexane-ethyl acetate (70–30 by volume) mixture. 14.2 g of 4-acetoxy-2α-benzoyloxy-5β,20-epoxy-1-hydroxy-9-oxo-7β,10β-bis(2,2,2-trichloroethoxy)carbonyloxy-11-taxen-13α-yl (2R,3S)-3-tert-butoxycarbonylamino-2-hydroxy-3-phenylpropionate are thus obtained.

Rf=0.29[cyclohexane-ethyl acetate (70–30 by volume)].

EXAMPLE 2

The ester obtained in Example 1 (11.9 g), then 200 cm³ of a methanol-acetic acid (1—1 by volume) mixture and finally 6 g of zinc powder are introduced, under an argon atmosphere, into a 3-necked, round-bottomed flask equipped with a stirrer. The mixture is heated for 2 hours at 60° C. and is then cooled to 25° C. After filtering, the precipitate is washed with 4 times 20 cm³ of a methanol-ethyl acetate (1—1 by volume) mixture. The filtrate and the washes are combined and then concentrated to dryness. The residue is taken up with 200 cm³ of toluene and then concentrated to dryness under reduced pressure (25 mm of mercury; 3.3 kPa at 35° C., then 1 mm of mercury; 0.13 kPa at 25° C.). The residue obtained is taken up with 200 cm³ of ethyl acetate. The solution is washed with 50 cm³ of a saturated sodium bicarbonate solution and then with 100 cm³ of distilled water. The organic phase is dried over magnesium sulphate. After filtering and concentrating to dryness under reduced pressure (25 mm of mercury; 3.3 kPa at 35° C., then 1 mm of mercury; 0.13 kPa at 25° C.), 10 g of 4-acetoxy-2α-benzoyloxy-5β,20-epoxy-1,7β,10β-trihydroxy-9-oxo-11-taxen-13α-yl (2R,3S)-3-tert-butoxycarbonylamino-2-hydroxy-3-phenylpropionate are obtained in the form of a white powder which is purified by chromatography on silica.

The product thus obtained has a purity greater than 99.5%.

EXAMPLE 3

16.6 cm³ of a 1N ethanolic solution of hydrochloric acid are added over 10 minutes, at a temperature of approximately 20° C., to a solution of 20.3 g (16.55 mmol) of 4-acetoxy-2α-benzoyloxy-5β, 20-epoxy-1-hydroxy-9-oxo-7β,10β-bis(2,2,2-trichloroethoxy) carbonyloxy-11-taxen-13α-yl (2R,3S)-3-tert-butoxycarbonylamino-2-(1-ethoxyethoxy)-3-phenylpropionate in 180 cm³ of absolute ethanol. After 30 minutes, the reaction mixture is concentrated to 4/5 of its volume. The oily residue obtained is slowly added to 200 cm³ of vigorously stirred water containing a sufficient quantity of sodium hydrogen carbonate to neutralize the excess hydrochloric acid. A pale yellow precipitate is formed. After filtering, washing with softened water and drying under reduced pressure, the crude product obtained (25 g) is purified on a silica column, eluting with a cyclohexane-ethyl acetate (70–30 by volume) mixture. 14.5 g of 4-acetoxy-2α-benzoyloxy-5β,20-epoxy-1-hydroxy-9-oxo-7β,10β-bis(2,2,2-trichloroethoxy)carbonyloxy-11-taxen-13α-yl (2R,3S)-3-tert-butoxycarbonylamino-2-hydroxy-3-phenylpropionate are thus obtained in the form of a white solid melting at 185° C. whose optical rotation is $[\alpha]_D = -32.4°$ (c=0.974; methanol).

EXAMPLE 4

To a solution of 5 g (4.33 mmol) of the ester obtained in Example 3 in 90 cm³ of an acetic acid-methanol (1—1 by volume) mixture heated to 50° C. in an inert atmosphere, 2.67 g (40.8 mmol) of activated zinc powder are added. The reaction mixture is stirred for 1 hour at 50° C. After cooling, the reaction mixture is filtered and the solid is washed with 10 cm³ of methanol. The combined filtrates are concentrated to dryness under reduced pressure at 30° C. The residue obtained is taken up with 50 cm³ of toluene and then concentrated to dryness again. The white meringue-like product obtained is dissolved in 100 cm³ of ethyl acetate. The solution obtained is washed with 25 cm³ of a 1M aqueous sodium hydrogen carbonate solution and then with 3 times 50 cm³ of water. After drying over sodium sulphate, filtering and concentrating to dryness, 3.34 g of a white solid are obtained. After recrystallizing from an ethanol-water mixture, 2.7 g of 4-acetoxy-2α-benzoyloxy-5β,20-epoxy-1,7β,10β-trihydroxy-9-oxo-11-taxen-13α-yl (2R,3S)-3-tert-butoxycarbonylamino-2-hydroxy-3-phenylpropionate are obtained in the form of a white solid melting at 196° C.

I claim:

1. Process for the preparation of a derivative of baccatin III or of 10-deacetylbaccatin III which is devoid of cytotoxicity, of formula:

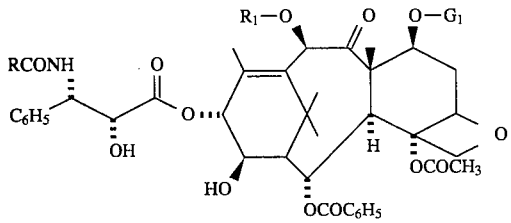

in which R represents a tert-butoxy or phenyl radical, $R_1$ represents an acetyl radical or a protecting group of the hydroxyl functional group in the form of an ether, ester or carbonate and $G_1$ represents a protecting group of the hydroxyl functional group in the form of an ether, ester or carbonate, in the 2'R,3'S or 2'S,3'S form, comprising treating a taxane derivative of formula:

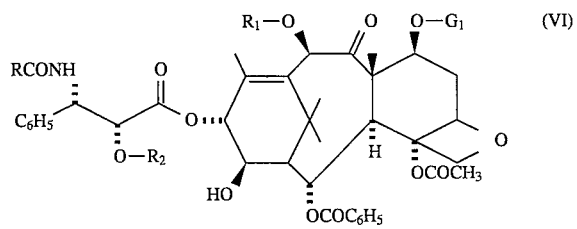

in which $R_1$ and $G_1$ are defined as above and $R_2$ represents a protecting group of the hydroxyl functional group selected from the methoxymethyl, 1-ethoxyethyl, benzyloxymethyl, (β-trimethylsilylethoxy)methyl or tetrahydropyranyl radicals, in acid medium by means of an alcoholic solution of an inorganic acid.

2. Process for the preparation according to claim 1 of a derivative of baccatin III or of 10-deacetylbaccatin III of formula (I) wherein R represents a tert-butoxy or phenyl radical and $R_1$ represents an acetyl or 2,2,2-trichloroethoxycarbonyl radical and $G_1$ represents a 2,2,2-trichloroethoxycarbonyl radical, in the 2'R,3'S or 2'S,3'S form.

3. Process for the preparation of a derivative of baccatin III or of 10-deacetylbaccatin III, of formula:

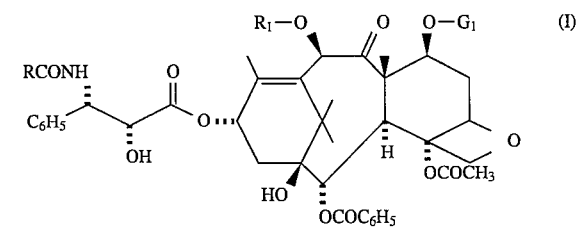

in which R represents a tert-butoxy or phenyl radical, $R_1$ represents an acetyl radical or a protecting group of the hydroxyl functional group in the form of an ether, ester or carbonate and $G_1$ represents a protecting group of the hydroxyl functional group in the form of an ether, ester or carbonate, in the 2'R,3'S or 2'S,3'S form, comprising treating a taxane derivative of formula:

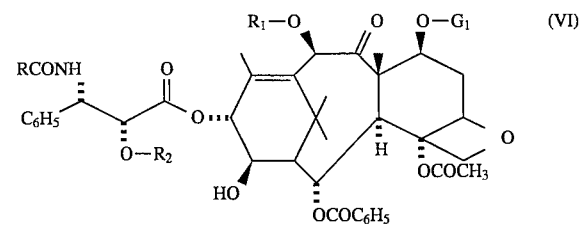

in which $R_1$ and $G_1$ are defined as above and $R_2$ represents a protecting group of the hydroxyl functional group selected from the methoxymethyl, 1-ethoxyethyl, benzyloxymethyl, (β-trimethylsilylethoxy)methyl or tetrahydropyranyl radicals, in acid medium by means of an ethanolic solution of hydrochloric acid.

4. Method for using a taxane derivative obtained by the process of claim 1 for the preparation of a taxane derivative of formula:

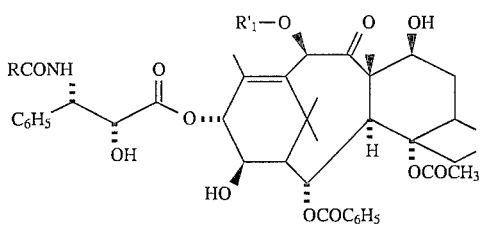

in which R represents a tert-butoxy or phenyl radical and R'₁ represents a hydrogen atom or an acetyl radical, comprising treating a taxane derivative obtained by the process of claim 1, optionally purified by chromatography or crystallization, under non-epimerizing conditions to remove a protecting group represented by $R_1$ and $G_1$.

5. Method for using a product obtained by the process of claim 2 for the preparation of a taxane derivative as defined in claim 4, comprising treating a taxane derivative obtained by the process of claim 2, optionally purified by chromatography or crystallization, with zinc in acetic acid in alcoholic medium at a temperature of between 20° C. and the reflux temperature of the reaction mixture and isolating the product obtained.

6. The process for the preparation of a derivative of baccatin III or of 10-deacetylbaccatin III of claim 1 wherein the treating in acid medium is conducted at a temperature of between about 0 and 30 degrees C.

7. The process for the preparation of a derivative of baccatin III or of 10-deacetylbaccatin III of claim 3 wherein R represents a tert-butoxy or phenyl radical and $R_1$ represents an acetyl or 2,2,2- trichloroethoxycarbonyl radical and $G_1$ represents a 2,2,2- trichloroethoxycarbonyl radical, in the 2'R,3'S or 2'S,3'S form.

8. A process for the preparation of a taxane derivative of formula (II):

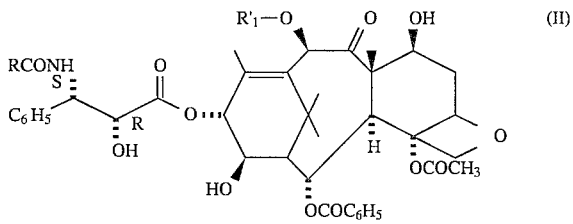

wherein R represents a tert-butoxy or phenyl radical and R'₁ represents a hydrogen atom or an acetyl radical, comprising the steps of:

(a) treating a taxane derivative of formula (VI):

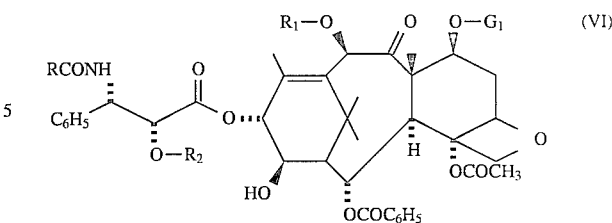

wherein R represents a tert-butoxy or phenyl radical, $R_1$ represents an acetyl radical or a protecting group of the hydroxyl functional group in the form of an ether, ester or carbonate, $R_2$ represents a protecting group of the hydroxyl functional group selected from the methoxymethyl, 1-ethoxyethyl, benzyloxymethyl, (β-trimethylsilylethoxy)methyl or tetrahydropyranyl radicals, and $G_1$ represents a protecting group of the hydroxyl functional group in the form of an ether, ester or carbonate in the 2'R,3'S or 2'S,3'S form; said step (a) treating being in an acid medium by means of an alcoholic solution of an inorganic acid to remove protecting group $R_2$ and provide a derivative of baccatin III or of 10-deacetylbaccatin III of formula (I):

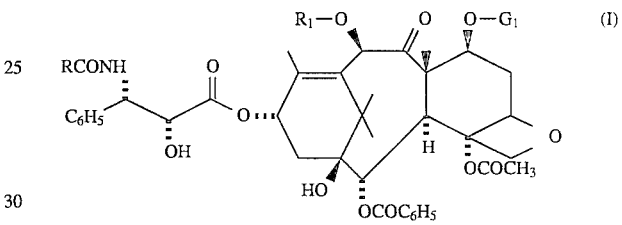

wherein R, $R_1$ and $G_1$ are defined as above, and wherein said derivative of formula (I) is devoid of cytotoxicity;

(b) purifying said derivative of formula (I) by chromatography or crystallization; and (c) treating said purified derivative of formula (I) under non-epimerizing conditions to remove the $R_1$ and $G_1$ protecting groups therefrom and provide said taxane derivative of formula (II).

9. The process for the preparation of a derivative of baccatin III or of 10-deacetylbaccatin III of claim 1 wherein the treating in acid medium is conducted at a temperature of between about 0° and 30 ° C.

10. The process for the preparation of a derivative of baccatin III or of 10-deacetylbaccatin III of claim 3 wherein R represents a tert-butoxy or phenyl radical and $R_1$ represents an acetyl or 2,2,2- trichloroethoxycarbonyl radical and $G_1$ represents a 2,2,2- trichloroethoxycarbonyl radical, in the 2'R, 3'S or 2'S,3'S form.

\* \* \* \* \*

UNITED STATES PATENT AND TRADEMARK OFFICE
CERTIFICATE OF CORRECTION page 1 of 4

PATENT NO. : 5,578,739
DATED : November 26, 1996
INVENTOR(S) : Augustin HITTINGER It is certified that error appears in the above-identified patent and that said Letters Patent is hereby corrected as shown below:

Claim 1, column 5, lines 45-54; and claim 4, column 7, lines 1-10, delete the formula

"                                                                    "

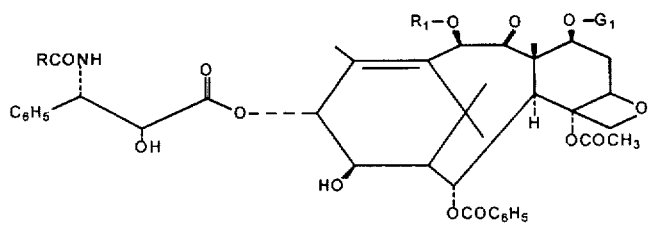

and insert therefor

--                                                                   --

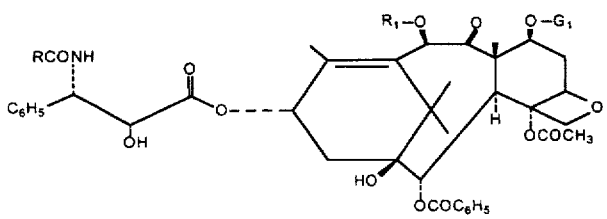

UNITED STATES PATENT AND TRADEMARK OFFICE
CERTIFICATE OF CORRECTION

PATENT NO. : 5,578,739
DATED : November 26, 1996
INVENTOR(S) : Augustin Hittinger It is certified that error appears in the above-identified patent and that said Letters Patent is hereby corrected as shown below:

Claim 1, column 5, line 58, "$G_t$" should read --$G_1$--.

Claim 1, column 6, lines 3-11; claim 3, column 6, lines 42-50; claim 8, column 8, lines 1-10; and in the specification, column 3, lines 20-28, delete the formula (IV)

"
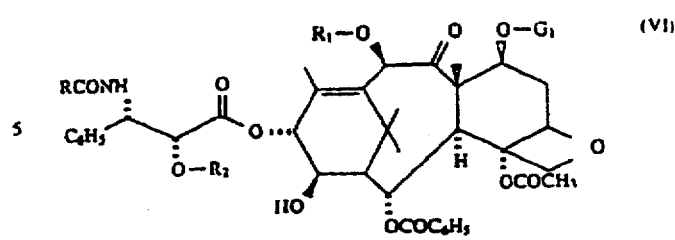
"

and insert therefor

--
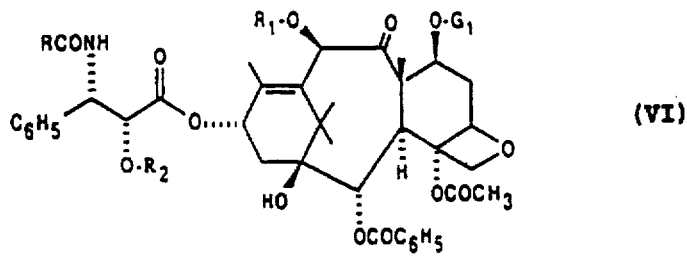
--

UNITED STATES PATENT AND TRADEMARK OFFICE
CERTIFICATE OF CORRECTION

PATENT NO. : 5,578,739
DATED : November 26, 1996
INVENTOR(S) : Augustin Hittinger It is certified that error appears in the above-indentified patent and that said Letters Patent is hereby corrected as shown below:

In Claim 8, column 7, lines 38-46; and in the specification, column 1, lines 45-54, delete formula II

"                                                                    "

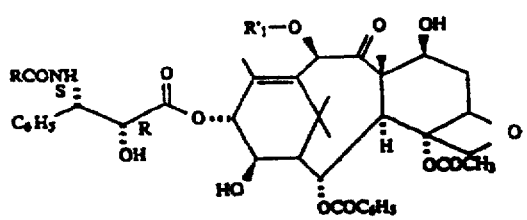

and insert therefor

--                                                                   --

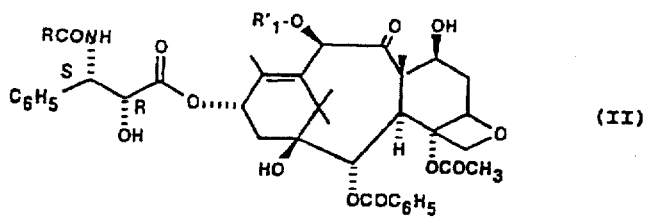

UNITED STATES PATENT AND TRADEMARK OFFICE
CERTIFICATE OF CORRECTION

PATENT NO. : 5,578,739
DATED : November 26, 1996
INVENTOR(S) : Augustin Hittinger It is certified that error appears in the above-indentified patent and that said Letters Patent is hereby corrected as shown below:

Title page, column 2, item [57], in the Abstract, delete formula (II)

"                                                                                                    "

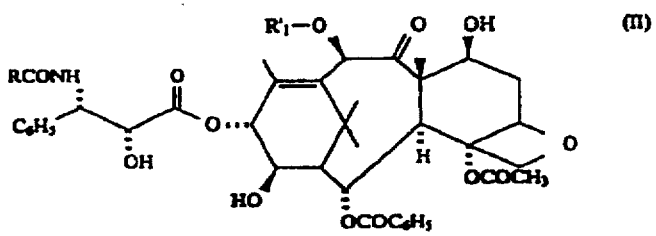

and insert therefor

--                                                                                                    --

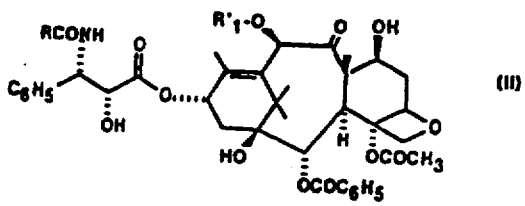

Signed and Sealed this

Twenty-first Day of September, 1999

Attest:

Q. TODD DICKINSON

*Attesting Officer*   Acting Commissioner of Patents and Trademarks